United States Patent [19]
LaCour et al.

[11] Patent Number: 6,022,968
[45] Date of Patent: Feb. 8, 2000

[54] PROCESSES FOR THE SYNTHESIS OF 5-(3-[EXO-BICYCLO[2.2.1]HEPT-2-YLOXY]-4-METHOXYPHENYL)-3,4,5,6-TETRAHYDROPYRIMIDIN-2(1H)-ONE

[75] Inventors: Thomas G. LaCour, Lafayette, Ind.; Charles William Murtiashaw, III, North Stonington, Conn.

[73] Assignee: Pfizer Inc, New York, N.Y.

[21] Appl. No.: 08/793,084

[22] PCT Filed: May 4, 1995

[86] PCT No.: PCT/IB95/00319

§ 371 Date: Aug. 18, 1997

§ 102(e) Date: Aug. 18, 1997

[87] PCT Pub. No.: WO96/04253

PCT Pub. Date: Feb. 15, 1996

Related U.S. Application Data

[63] Continuation-in-part of application No. 08/286,579, Aug. 5, 1994, abandoned.

[51] Int. Cl.$^7$ .................................................. C07D 239/10
[52] U.S. Cl. ............................................................ 544/318
[58] Field of Search .............................................. 544/318

[56] References Cited

U.S. PATENT DOCUMENTS 5,270,206  12/1993  Saccomano et al. .................... 435/280

FOREIGN PATENT DOCUMENTS

WO 8706576  11/1987  WIPO .
WO 9412461  6/1994  WIPO .

OTHER PUBLICATIONS

V. Askam et al., "Compounds Having Antitremorine Activity, Bicarbamate Derivatives of 1,3–Diamino–2–Phenylpropanes," *Chemical Abstracts*, vol. 92, No. 13, Abstract No. 110633r (1980).

V. Askam et al., "Compounds Having Antitremorine Activity; Biscarbamate Derivatives," *J. Chem. Research (S)*, vol. 7, p. 234 (1979).

H. Römpp, *Römpps Chemie–Lexicon*, 9th Ed., vol. 3, p. 1825 (1990).

Müller et al., *Methoden der Organischen Chemie*, 4th Ed., vol. E4, pp. 183–187, 372–373 (Houben–Weyl 1952–).

*Primary Examiner*—Richard L. Raymond
*Attorney, Agent, or Firm*—Peter C. Richardson; Paul H. Ginsburg; Roy F. Waldron

[57] ABSTRACT

This invention relates to novel processes for preparing the pharmaceutically active compound 5-(3-[(2S)-exo-bicyclo[2.2.1]hept-2-yloxy]-4-methoxyphenyl)3,4,5,6 tetrahydropyrimidin-2(1H)-one and its corresponding 2R enantiomer and for preparing certain intermediates used in the synthesis of these compounds. It also relates to novel intermediates used in the synthesis of such pharmaceutically active compounds and to other novel compounds that are related to such intermediates.

14 Claims, No Drawings

PROCESSES FOR THE SYNTHESIS OF 5-(3-[EXO-BICYCLO[2.2.1]HEPT-2-YLOXY]-4-METHOXYPHENYL)-3,4,5,6-TETRAHYDROPYRIMIDIN-2(1H)-ONE

The present application is a 371 of PCT/IB95/00319, filed May 4, 1995 which is a CIP of U.S. application Ser. No. 08/286,579, filed Aug. 5, 1994, now abandoned.

BACKGROUND OF THE INVENTION

This invention relates to novel processes for preparing the pharmaceutically active compound 5-(3-[(2S)-exo-bicyclo[2.2.1]hept-2-yloxy]-4-methoxyphenyl)3,4,5,6 tetrahydropyrimidin-2(1H)-one and its corresponding 2R enantiomer and for preparing certain intermediates used in the synthesis of these compounds. It also relates to novel intermediates used in the synthesis of such pharmaceutically active compounds and to other novel compounds that are related to such intermediates.

International Patent Application WO 87/06576, which was published on Nov. 5, 1987, refers to 5-(3-[(2-exo-bicyclo[2.2.1]hept-2-yloxy]-4-methoxyphenyl)-3,4,5,6tetrahydropyrimidin-2(1H)-one, and states that it is useful as an antidepressant. International Patent Application WO 91/07178, which was published on May 30, 1991, refers to the utility of this compound in the treatment of asthma, inflammatory airway diseases and skin diseases.

U.S. Pat. No. 5,270,206, which issued on Dec. 14, 1993, refers to a process for preparing (+)-(2R)-endo-norborneol (also referred to as (2R)-endo-bicyclo[2.2.1]heptan-2-ol or (1S, 2R, 4R)-bicyclo[2.2.1]heptan-2-ol) and (−)-(2S)-endo-norborneol (also referred to as (2S)-endo-bicyclo[2.2.1]heptan-2-ol or (1R, 2S, 4S)-bicyclo[2.2.1]heptan-2-ol), and to their further conversion into the pharmaceutically active agents 5-(3-[(2S)-exo-bicyclo[2.2.1]hept-2-yloxy]-4-methoxyphenyl)-3,4,5,6-tetrahydropyrimidin-2(1H)-one, depicted below,

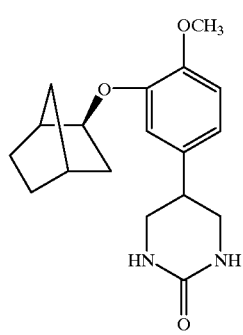

VI and 5-(3-[(2R-exo-bicyclo[2.2.1]hept-2-yloxy]-4-methoxyphenyl)-3,4,5,6-tetrahydropyrimidin-2(1H)-one, depicted below,

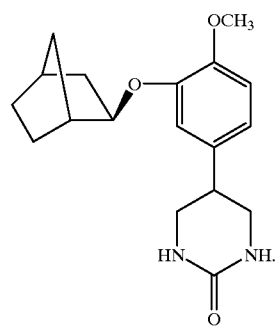

VI'

All documents cited herein, including the foregoing, are incorporated herein by reference in their entireties.

SUMMARY OF THE INVENTION

This invention relates to a compound having the formula

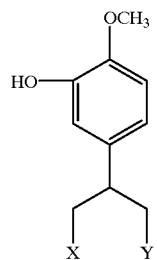

(II)

wherein X and Y are the same and are selected from —CN, —CO$_2$(C$_1$–C$_6$)alkyl, —CONH$_2$ and —CONHOH, or X and Y, taken together, form a group of the formula

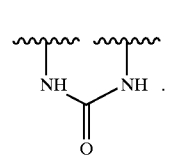

(a)

This invention also relates to a compound having the formula

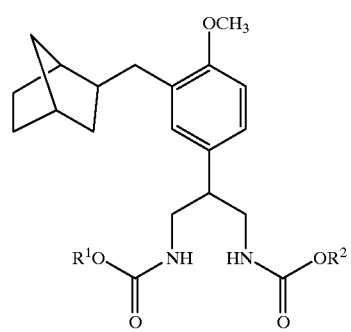

(V)

wherein R$^1$ and R$^2$ are independently selected from (C$_1$–C$_6$) alkyl and hydrogen.

This invention also relates to compounds of the formulae

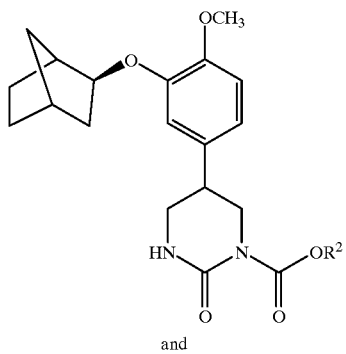

(VIII)

and

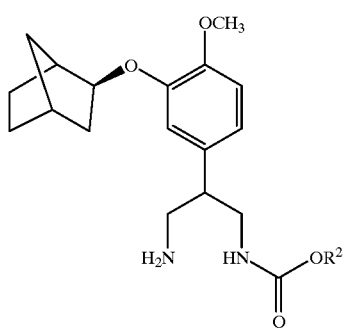

(VII)

wherein each $R^2$ is independently selected from $(C_1-C_6)$ akyl.

This invention also relates to a process for preparing a compound of the formula

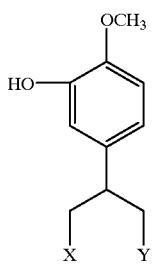

(II)

wherein X and Y are the same and are selected from —CN, —CO$_2$(C$_1$–C$_6$)alkyl, —CONH$_2$ and —CONHOH, or X and Y, taken together, form a group of the formula

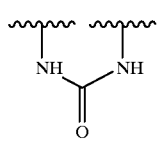

(a)

comprising: (1) reacting 3-hydroxy-4-methoxybenzaldehyde with a compound of the formula XCH$_2$CO$_2$H, wherein X is defined as above, in the presence of a base, preferably a tertiary amine, to yield a compound of the formula II wherein X and Y are both —CN, —CO$_2$(C$_1$–C$_6$)alkyl, —CONH$_2$ or —CONHOH; or (2) (a) reacting a compound of the formula II wherein X and Y are both —CN with hydrogen peroxide, preferably basic aqueous hydrogen peroxide, to form the corresponding bis-amide in which both —CN groups are replaced by —CONH$_2$; (b) subjecting the bis-amide formed in step (a) to a Hoffman rearrangement using an oxidizing agent (e.g., bis(acetoxy)iodobenzene, bis(trifluorocetoxy)iodobenzene, NaOCl, NaOBr or lead tetraacetate) to form the corresponding biscarbamate; and (c) reacting the biscarbamate formed in step (b) with a base (e.g., an alkali metal alkoxide containing from one to six carbon atoms or an alkali metal hydroxide), to form a cyclic urea wherein X and Y, taken together, form a group of the formula "a", as depicted above.

This invention also relates to a process for preparing a compound of the formula

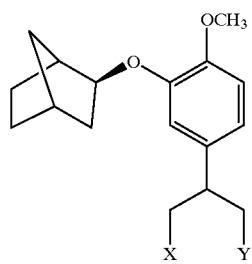

(III)

or

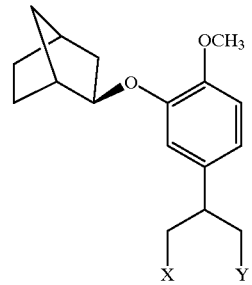

(III')

wherein X and Y are defined as for formula II above, comprising reacting a compound of formula II, as defined above, with, respectively, R-(+)-endo-norbomeol or S-(−)-endo-norbomeol, a triaryl or trialkyl phosphine and an azo dicarboxylate.

This invention also relates to a process for preparing a compound of the formula

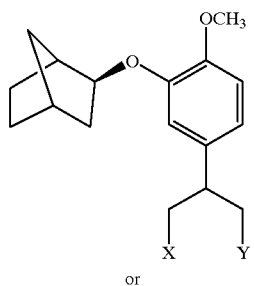

(III)

or

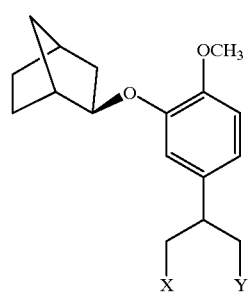

(III')

wherein X and Y are the same and are selected from —CN, —CONH₂, CO₂(C₁–C₆)alkyl and —CONHOH, or X and Y, taken together, form a group of the formula

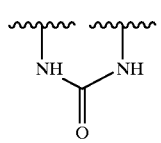

(a)

comprising: (1) reacting 3-hydroxy-4-methoxybenzaldehyde with a compound of the formula XCH₂CO₂H, wherein X is —CN, —CO₂(C₁–C₆)alkyl, -CONH₂ or —CONHOH, in the presence of a base, preferably a tertiary amine, to form a compound of the formula

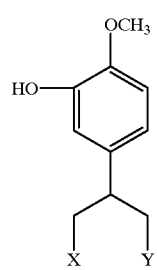

(II)

wherein X and Y are the same and are selected from —CN, —CONH₂, —CO(C₁–C₆)alkyl and —CONHOH; or (2) (a) reacting a compound of the formula II wherein X and Y are both —CN with hydrogen peroxide to form the corresponding bis-amide in which both —CN groups are replaced by —CONH₂; (b) subjecting the bis-amide formed in step (a) to a Hoffman rearrangement using an oxidizing agent (e.g., bis(acetoxy)iodobenzene, bis(trifluorocetoxy)iodobenzene, NaOCl, NaOBr or lead tetraacetate) to form the corresponding biscarbamate; and (c) reacting the biscarbamate formed in step (b) with a base (e.g., an alkali metal alkoxide containing from one to six carbon atoms), to form a cyclic area wherein X and Y, taken together, form a group of the formula

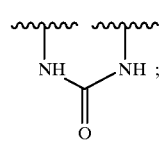

(a)

and then (3) reacting said compound of formula II so formed in step 1 or 2 above with, respectively, R-(+)-endo-norborneol or S-(−)-endo-norborneol, a triaryl or trialkyl phosphine and an azo dicarboxylate.

This invention also relates to a process for preparing a compound of the formula

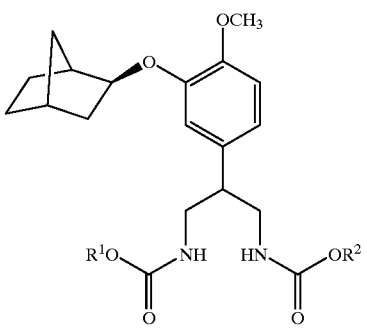

(V)

or

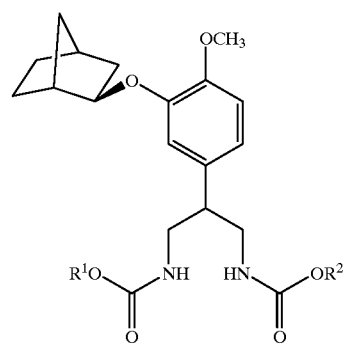

(V')

wherein R¹ and R² are independently selected from hydrogen and (C₁–C₆)alkyl, comprising reacting, respectively, a compound of the formula

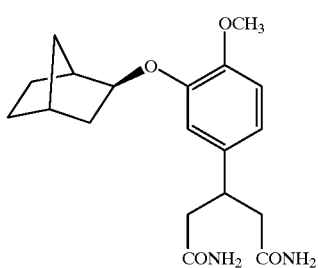
(IV)

or

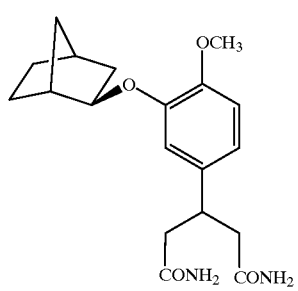
(IV')

with diacetoxyiodobenzene, NaOZ and Z'OH, wherein Z and Z' are independently selected from hydrogen and $(C_1-C_6)$alkyl.

This invention also relates to a process for preparing a compound of the formula

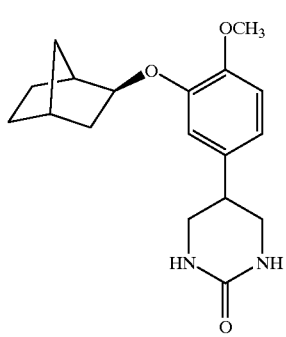
(VI)

or

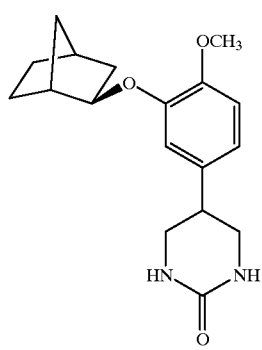
(VI')

comprising reacting, respectively, a compound of the formula

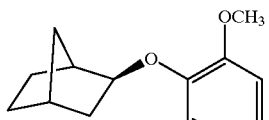
(V)

or

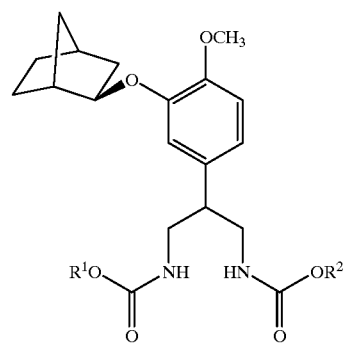
(V')

wherein $R^1$ and $R^2$ are independently selected from hydrogen and $(C_1-C_6)$alkyl with compounds of the formulae NaOZ and Z'OH, wherein Z and Z' are independently selected from hydrogen and $(C_1-C_6)$alkyl.

This invention also relates to a process for preparing a compound of the formula

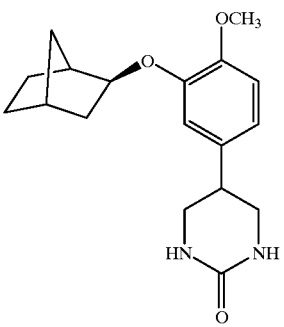
(VI)

or

-continued (VI')

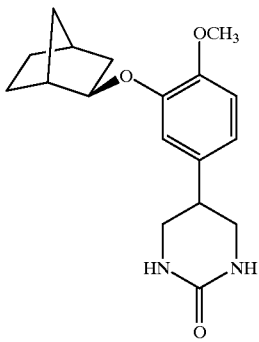

(V')

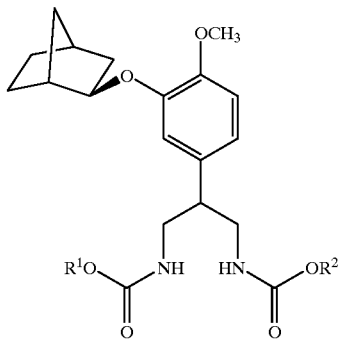

wherein $R^1$ and $R^2$ are independently selected from hydrogen and $(C_1-C_6)$alkyl; and then either (b1) isolating said intermediate of formula V or V' and reacting it with compounds of the formulae NaOZ and Z'OH, wherein Z and Z' are defined as above; or (b2) reacting said intermediate of formula V or V' in situ with compounds of the formula NaOZ and Z'OH, wherein Z and Z' are defined as above.

As used herein, the expression "reaction inert solvent" refers to a solvent which does not interact with starting materials, reagents, intermediates or products in a manner which adversely affects the yield of the desired product or products.

The term "alkyl", as used herein, unless otherwise indicated, includes saturated monovalent hydrocarbon radicals having straight, branched or cyclic moieties or combinations thereof.

Formulae II, and V and V' above include compounds identical to those depicted but for the fact that one or more hydrogen, carbon, nitrogen or oxygen atoms are replaced by radioactive or stable isotopes thereof. Such radiolabelled compounds are useful as research and diagnostic tools in metabolism pharmacokinetic studies and in binding assays.

DETAILED DESCRIPTION OF THE INVENTION

The processes of the this invention and methods of preparing the novel compounds of this invention are described in the following reaction schemes and discussion. Unless otherwise indicated, the substituents X, Y, R, $R^1$, $R^2$, $R^3$, and $R^4$, group "(a)" and formulae II, III, III', IV, IV', V, V', VI and VI' in the reaction schemes and discussion that follow are defined as above.

comprising:

reacting, respectively, a compound of the formula (IV)

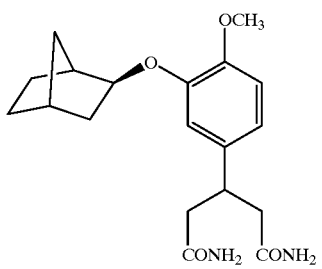

or (IV')

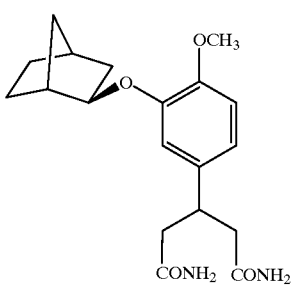

with diacetoxyiodobenzene, NaOZ and Z'OH, wherein Z and Z' are independently selected from hydrogen and $(C_1-C_6)$alkyl, to form an intermediate of the formula (V)

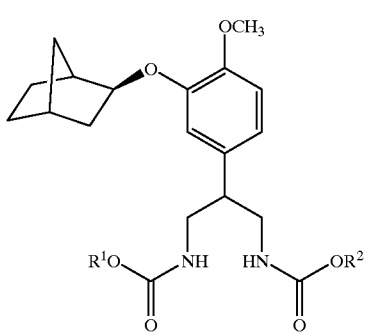

or

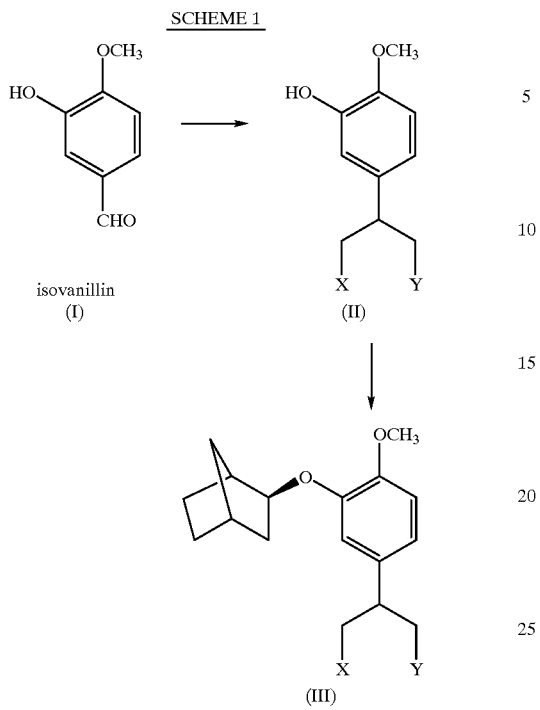
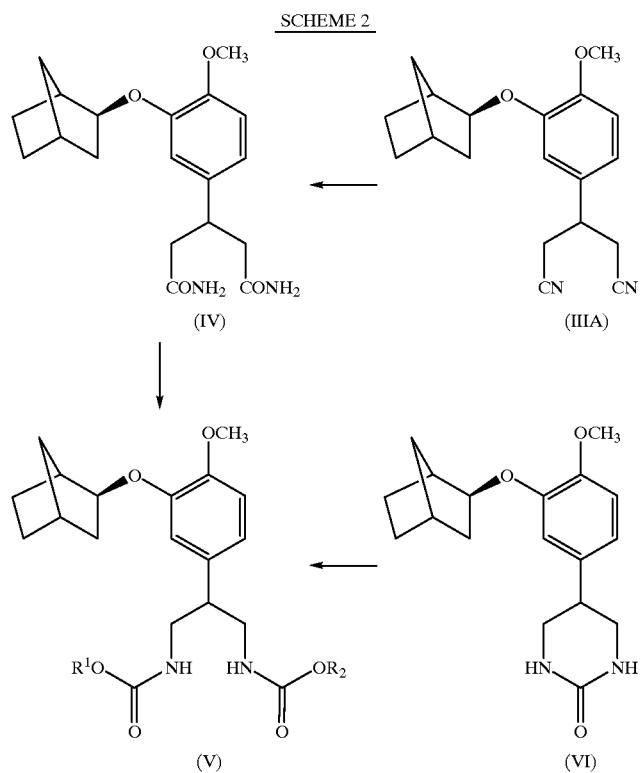

SCHEME 2A
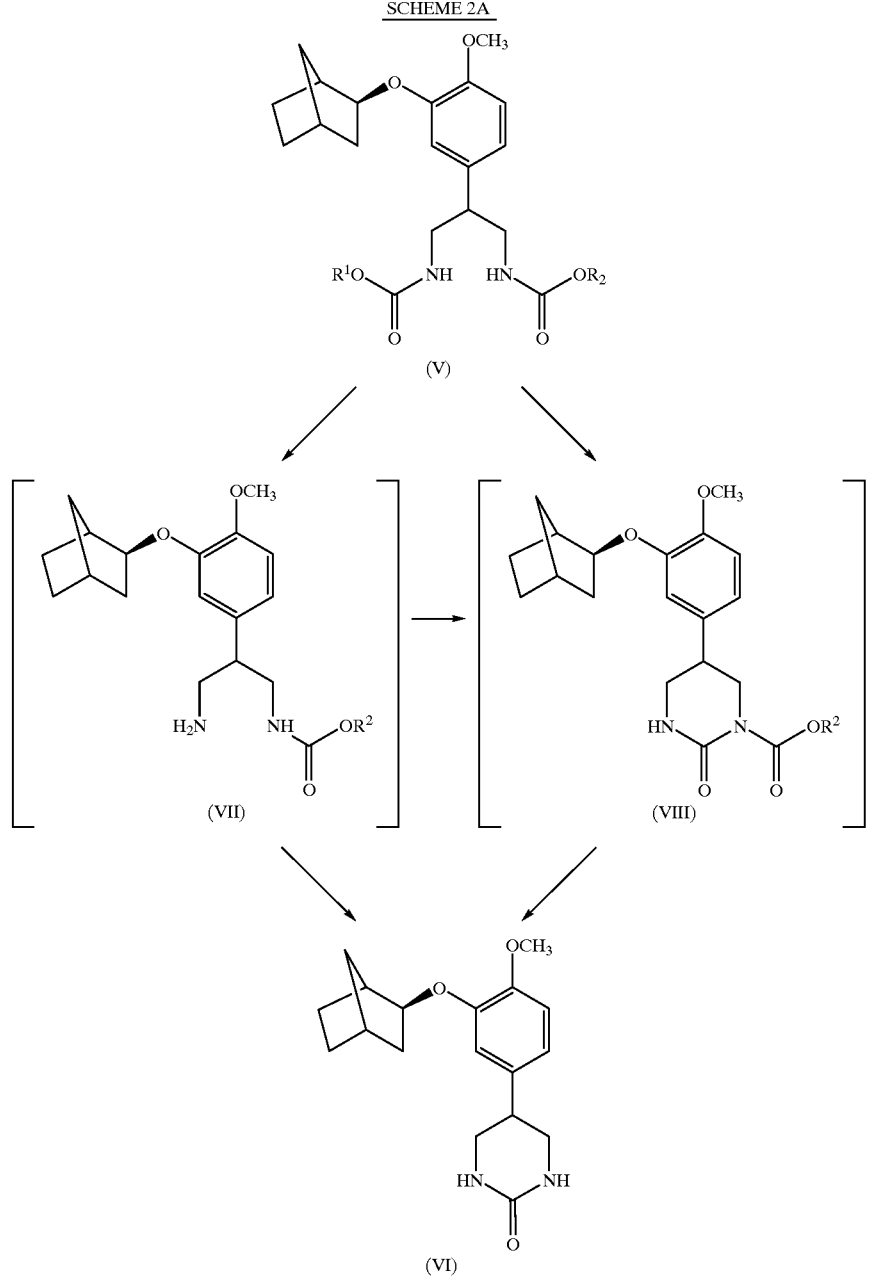

SCHEME 3

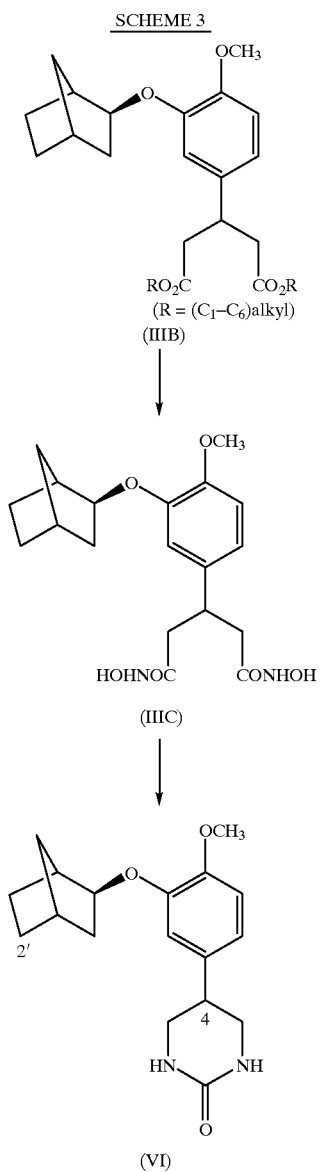

Scheme 1 illustrates the preparation of compounds of the formulae II and III. Scheme 2 illustrates the preparation of compounds of the formula V and also the preparation of 5-(3-[(2S)-exo-bicyclo[2.2.1]hept-2-yloxy]-4-methoxyphenyl)-,4,5,6-tetrahydropyrimidin-2-(1H)-one (compound VI) from the compound of formula II wherein X and Y are both —CN. (Such compound of formula II wherein X and Y are both —CN is referred to in scheme 2 and hereinafter as the compound of formula IIIA.) Scheme 3 illustrates the preparation of compound VI from compounds of the formula III wherein X and Y are both —CO$_2$(C$_1$–C$_6$)alkyl or —CONHOH. (The compound of formula III wherein X and Y are both —CO$_2$(C$_1$–C$_6$)alkyl or —CONHOH are referred to in scheme 3 and hereinafter, respectively, as the compound of formula IIIB or IIIC).

Referring to scheme 1, isovanillin (compound 1) is condensed with two molar equivalents of a compound of the formula XCH$_2$CO$_2$H, wherein X is —CN, —CO$_2$(C$_1$–C$_6$) alkyl, —CONH$_2$ or —CONHOH, in a sequential Knoevenagel-Michael sense with accompanying decarboxylation, to yield a compound of the formula II, wherein X and Y are the same and are selected from the values given in the above definition of X, in a reaction inert solvent in the presence of a base, preferably a tertiary amine. This reaction may be conducted at a temperature ranging from about 10° C. to about 130° C. It is preferably conducted at about the reflux temperature. Suitable solvents include but are not limited to N-methylmorpholine, triethylamine, pyridine, as well as non-basic reaction-inert solvents such as tetrahydrofuran (THF), dimethylformamide (DMF), acetonitrile and toluene. Preferably, a secondary amine (e.g., piperidine or pyrrolidine) is also added as a catalyst. In one preferred embodiment of the reaction, N-methylmorpholine is used as the solvent/base and piperidine is also added to the reaction mixture.

Compounds of the formula II wherein X and Y, taken together, form a group of the "a" (ie., the cyclic urea) may be prepared by subjecting the compound of formula II wherein X and Y are both —CN to the series of reactions illustrated in scheme 2 and described later in this application.

The compound of formula II formed in the above reaction can be converted into the corresponding compound of the formula III by coupling it under Mitsunobu conditions with either R-(+)-endo-norborneol, depicted below,

or S-endo-norborneol, depicted below

to yield, respectively, the corresponding compound of formula III or III' having the opposite stereochemistry as determined by the endo-norbomeol reactant. Thus, if R-endo-norbomeol is used, the product will be a compound of the formula III that has an "S" configuration, and if S-endo-norborneol is used, the product will be a compound of the formula III' that has an "R" configuration.

This reaction is typically carried out in the presence of a triaryl or trialkyl phosphine such as triphenylphosphine or tributylphosphine and an azo dicarboxylate oxidizing agent. It is also generally carried out in an aprotic solvent such as tetrahydrofuran (THF) acetonitrile, methylene chloride, DMF, toluene and benzene, preferably THF, at a temperature from about 10° C. to about 150° C., preferably at about the reflux temperature. Suitable azo compounds include diisopropylazodicarboxylate, azodicarbonyldipiperldine and diethylazodicarboxylate. Diisopropylazodicarboxylate and azodicarbonyidipiperidine are preferred.

The stereochemistry of the compound of formula III or III' formed in the above step is retained in all subsequent steps shown in schemes 2 and 3.

As indicated above, scheme 2 illustrates the conversion of compounds of the formula IIIA into compounds of the formula VI. Referring to scheme 2, a compound of the formula IIIA is hydrolyzed with hydrogen peroxide, preferably basic aqueous hydrogen peroxide, to form the bisamide of formula IV. This reaction is typically conducted in a polar solvent such as acetone, ethanol, isopropanol or methyl ethyl ketone, with acetone being preferred, at atemperature from about 0° C. to about 100° C., with about room temperature being preferred. Sodium carbonate or another inorganic salt of similar basicity may be added to the reaction mixture to accelerate the reaction.

The compound of formula IV so formed is then subjected to a Hoffman rearrangement reaction in which both carboxamide groups are converted, with migration of nitrogen, into the carbamate groups of formula V. Suitable oxidizing reagents include bis(acetoxy)iodobenzene, bis (trifluoroacetoxy)iodobenzene, NaOCl, NaOBr and lead tetracetate may be used. Bis(acetoxy)iodobenzene is preferred. This reaction is typically carried out in the presence of a base. When diacetoxyiodobenzene is used, acceptable bases include alkali metal hydroxides and $(C_1-C_6)$alkoxides. The reaction temperature may range from about $-20°$ C. to about $100°$ C., with from about $0°$ C. to about $25°$ C. being preferred. Examples of appropriate reaction-inert solvents are $(C_1-C_6)$alkanols, THF, DMF and acetonitrile.

The final step in the sequence is the base catalyzed closure of the biscarbamate of formula V to form the symmetrical pyrimidin-2-one of formula VI. This reaction may be carried out from about 0° C. to about 100° C., and is preferably carried out at the reflux temperature. Suitable solvents include but are not limited to lower alcohols, with methanol being preferred. Suitable bases include alkali metal alkoxides containing from one to six carbon atoms. The preferred base is sodium methoxide.

Alternatively, the last two steps of the sequence may be accomplished in a combined fashion without the isolation of the bis-carbamate V. This modification is essentially identical to the previous description of the Hoffman rearrangement. It is preferable to conduct the reaction at the reflux temperature of the solvent. It is also preferable to add additional base to the reaction mixture. The range of acceptable oxidizing agents, bases and solvents is the same as described previously. The preferred reaction utilizes diacetoxyiodobenzene, sodium methoxide and methanol.

The reaction of compounds of the formula V to form compounds of the formula VI, as described above, may proceed through one or both of the intermediates of formulae VII and VIII shown in scheme 2A.

The compound of formula III wherein X and Y are both —$CONH_2$ is the same as the compound of formula IV, and therefore it can be converted into compound (VI) using the methods Illustrated in scheme 2.

Compounds of the formula III wherein X and Y are both —CONHOH or —$CO_2(C_1-C_6)$alkyl may be converted into compound VI using the methods illustrated in scheme 3.

Referring to scheme 3, the diester of formula IIIB is reacted with hydroxylamine hydrochloride in the presence of a base, e.g., a tertiary amine base, to form the hydroxamic acid of formula IIIC. This reaction can be conducted in a variety of reaction-inert solvents that do not have a strong nucleophilic character, including but not limited to lower alcohols, cyclic and acyclic ethers (e.g., ethyl ether or THF), neutral aromatic compounds such as benzene and toluene, DMF, dimethylacetamide, ethyl acetate, acetonitrile and water, at a temperature from about 0° C. to about 100° C., preferably at about 20° C.

The hydroxamic acid of formula IIIC can then be converted into compound VI via a Loessen rearrangement using conditions or a reagent having the ability to dehydrate an alcohol, at a temperature from about 0° to about 100° C., preferably at about 20° C. The preferred reagent is p-toluenesulfonylchloride. Alternatively, one can form a different ester of the hydroxamic acid, optionally in situ, and then convert that ester via heat and/or acid treatment into the compound of formula VI, using methods well known in the art.

The preparation of other compounds of the present invention not specifically described in the foregoing experimental section can be accomplished using combinations of the reactions described above that will be apparent to those skilled in the art.

In each of the reactions discussed or illustrated in the scheme above, pressure is not critical unless otherwise indicated. Pressures from about 0.5 atmospheres to about 3 atmospheres are generally acceptable, and ambient pressure, i.e., about 1 atmosphere, is preferred as a matter of convenience.

The processes and products of this invention are useful in the synthesis of the pharmaceutically active compounds VI and VI'. Compounds VI and VI', as well as racemic mixtures of these compounds (hereinafter referred to, collectively as "the active compounds") are useful in the treatment of depression, asthma, inflammatory airway disorders and skin disorders (e.g., psoriasis and atopic dermatitis).

The active compounds are calcium independent c-AMP phosphodiesterase inhibitors. The ability of such compounds to Inhibit c-AMP phosphodiesterase may be determined by the method of Davis, *Biochimica et Biophysics. Acta.,* 797, 354–362 (1984).

The antidepressant activity of the active compounds may be determined by the behavioral despair paradigm described by Porsult et al., *Arch. Int. Pharmacodyn.,* 227, 327–336 (1977) and by the procedure described by Roe et at., *J. Pharmacol. Exp. Therap.,* 226, 686–700 (1983) for determining the ability of a test drug to counteract reserpine hypothermia in mice.

When used for the treatment of depression the active compounds are used as is or in the form of pharmaceutical compositions comprising an active compound and pharmaceutically-acceptable carriers or diluents. For oral administration, the preferred route for administering the active compounds, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules preferred materials therefor include lactose or milk sugar and high molecular weight polyethylene glycols.

For oral administration, the daily dose of active agent is from about 0.1 mg to about 10 mg, and for parenteral administration, preferably i.v. or i.m., from about 0.01 mg. to about 5 mg. The prescribing physician, of course, will ultimately determine the appropriate dose for a given human subject dependent upon factors such as the severity of the patient's symptoms and the patients response to the particular drug.

In vitro and in vivo tests relevant to the utility of the active compounds in treating asthma and skin disorders are discussed in International Patent Application WO 91/07178, referred to above and incorporated herein by reference in its entirety, on pages 4 and 5 of the specification and in Examples 1–3.

In the systemic treatment of asthma or inflammatory skin diseases with one of the active compounds, the dosage is generally from about 0.01 to 2 mg/kg/day (0.5–100 mg/day in a typical human weighing 50 kg) in single or divided doses, regardless of the route of administration. Of course, depending upon the exact compound and the exact nature of the individual illness, doses outside this range will be prescribed at the discretion of the attending physician. In the treatment of asthma, intranasal (drops or spray), inhalation of an aerosol through the mouth, and conventional oral administration are generally preferred. However, if the patient is unable to swallow, or oral absorption is otherwise impaired, the preferred systemic route of administration will be parenteral (i.m., i.v.). In the treatment of inflammatory skin diseases, the preferred route of administration is oral or topical. In the treatment of inflammatory airway diseases, the preferred route of administration is intranasal or oral.

The active compounds are generally administered in the form of pharmaceutical compositions comprising one of said compounds together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; for topical administration, in the form of solutions, lotions, ointments, salves and the like, in general containing from about 0.1 to 1% (w/v) of the active ingredient; and for intranasal or inhaler administration, generally as 0.1 to 1% (w/v) solution.

The present invention is illustrated by the following examples. It will be understood, however, that the invention is not limited to the specific details of these examples.

EXAMPLE 1

3-(3-Hydroxy-4-methoxyphenyl)-pentane-1,5-dinitrile

To a 500 mL flask containing isovanillin (30.4 gm, 200 mmol) and cyanoacetic acid (68.0 gm, 800 mmol) was charged a solution consisting of 3.0 mL (30 mmol) piperidine and 151 mL N-methylmorpholine. The initially formed yellow slurry was warmed to mild reflux for 21 hours and then cooled to room temperature and concentrated on a rotary evaporator. The resulting brown oil was dissolved in 430 mL ethyl acetate (EtOAc), washed sequentially with water ($H_2O$), five normal hydrochloric acid (5N HCl) and $H_2O$ and the combined aqueous washes back extracted with dichloroethane. Combination of the organic layers followed by solvent removal led to a thick orange oil which was crystallized from ethyl acetate/methylene chloride (EtOAc/$CH_2Cl_2$) to yield 38.3 gm of orange solids after filtration and drying. Recrystallization from EtOAc/diisopropyl ether gave 35.3 gm (82%) of light yellow solid, m.p. 90–92° C.

EXAMPLE 2

3-(3-[(2S)-exo-Bicyclo[2.2.1]hept-2-yloxy]-4-methoxyphenyl)-1,5-pentanedinitrile To a tetrahydrofuran (THF) solution (20 mL) containing R-(+)-endo-norbomeol (1.12 gm, 10.0 mmol), 3-(3-hydroxy-4-methoxyphenyl)-pentane-1,5-dinitrile (4.33 gm, 20 mmol) and triphenylphosphine (TPP) (3.93 gm, 15 mmol) was added 1,1'-(azodicarbonyl)-dipiperldine (ADDP) (3.78 gm, 15 mmol) at room temperature. The resulting brown slurry was heated at reflux for 12 hours, and then diluted with 10 mL THF and 30 mL toluene, cooled to room temperature and granulated for 30 minutes. After filtration to remove the reduced ADDP, the filtrate was washed 2X with 20 ml 1N sodium hydroxide (NaOH) and the remaining organic phase stirred with 0.2 gm activated charcoal and 20 gm sodium sulfate ($Na_2SO_4$), filtered and concentrated to a thick, dark brown oil. Recrystallization from isopropanol/hexanes gave 2.34 gm (75%) of an off-white solid, m.p. 126–127° C.

EXAMPLE 3

3-(3-[(2S)-exo-Biocyclo[2.2.]hept-2-yloxy]-4-methoxyphenyl)-pentane-1.5-dinitrile To a refluxing solution of THF (30 mL) containing norbomeol (2.243 gm, 20.00 mmol) and triphenylphosphine (5.272 gm, 20.10 mmol) was added a second THF solution of 3-(3-hydroxy-4-methoxyphenyl)-pentane-1,5-dinitrile (4.350 gm, 20.10 mmol) and diisopropyl azodicarboxylate (DIAD) (4.044 gm, 21.00 mmol). The mixture was heated at reflux for 18 hours, cooled and concentrated on the rotary evaporator, and then redissolved in 60 mL toluene. The resulting brown toluene solution was washed 2 times with 1N NaOH, dried over $Na_2SO_4$, and filtered and concentrated to yield 18 gm of beige solid. Recrystallization from 1/1 isopropanol/hexanes gave 4.26 gm (69%) of white solid, m.p. 127–128° C.

EXAMPLE 4

3-(3-[(2S)-exo-Bicyclo]2.2.1hept-2-yloxyl-4-methoxyphenyl)qlutaramide

To a cooled (6° C.) acetone solution (46 mL) of 3-(3-[(2S)-exo-bicyclo[2.2.1]hept-2-yloxy]-4-methoxyphenyl)-pentane-1,5-dinitrile (2.29 gm, 7.38 mmol) was added 24 mL of 10% aqueous sodium carbonate ($Na_2CO_3$) (23 mmol) followed by 5.2 mL of 30% hydrogen pyroxide ($H_2O_2$). The resulting slurry was stirred at room temperature for 4 days, treated with an additional 1.7 mL 30% H₂O₂ and then stirred for two more days. The excess peroxide was decomposed by the addition of 4 equivalents of sodium bisulfite (NaHSO₃) and the volume was reduced to about 80 mL on the rotary evaporator. The thick slurry was then acidified using 6.5 mL of concentrated HCl, neutralized with concentrated ammonium hydroxide (NH₄OH) and condensed to about 50 mL of volume. Filtration and vacuum drying provided 2.20 gm (86%) of white solids, m.p. 161–163° C.

EXAMPLE 5

5-(3-[(2S)-exo-Bicyclo[2.2.1]hept-2-yloxy]-4-methoxyphenyl)-3.4.5.6-tetrahydropyrinidin-2(1H)-one To a cooled (2°) methanol (MeOH) (40 mL) suspension of diacetoxyiodobenzene (43.60 gm, 133 mmol) was added 152 mL of 25% sodium methoxide (NaOMe) in MeOH solution over 10 minutes. After stirring for 20 minutes at 3° C., 3-(3-[(2S)-exo-bicyclo[2.2.1]hept-2-yloxy]-4-methoxyphenyl)glutaramide (22.98 gm, 66.5 mmol) was added as a precooled slurry in 45 mL MeOH and the reaction was allowed to warm to room temperature over 3 hours followed by 45 minutes of heating at reflux. The slurry was cooled to room temperature, treated with 152 mL of 25% NaOMe in MeOH solution and heated to reflux for 16 hours. The condenser was then replaced with a distillation head and 350 mL of MeOH was removed. The resulting slurry was cooled to 12° C., diluted with 200 mL CH₂Cl₂ and 100 ml H₂O and neutralized with concentrated HCl. Separation of the layers and extraction of the aqueous layer 2X with CH₂Cl₂ provided 3 organic layers which were combined, dried over sodium sulfate (Na₂SO₄), filtered and then concentrated to yield 39 gm of pale orange solid. Reslurry in refluxing EtOAc gave 15.48 gm of white solid (77%) m.p. 199–200° C.

EXAMPLE 6

N,N'-Dimethoxycarbonyl-2-(3-[(2S)-exo-bicyclo[2.2.1]hept-2-yloxy]-4-methoxyphenyl)-1,3-propanediamine To a cooled (0°C.) suspension of 3-(3-[(2S)-exo-bicyclo[2.2.1]hept-2-yloxy]-4-methoxyphenyl)-glutaramide (0.346 gm, 1.00 mmol) in 1.75 ml of MeOH was added 0.140 gm of potassium hydroxide (KOH) (2.50 mmol) followed by 0.657 gm (3.0 mmol) diacetoxyiodobenzene. The resulting hazy yellow solution was allowed to warm to room temperature, stir for 80 minutes and was then concentrated on the rotary evaporator to a paste. The material was transferred to a separatory funnel with water and extracted two times with CH₂Cl₂. The combined organic layers dried over Na₂SO₄, filtered and concentrated to provide 0.506 gm (125%) of the desired bis-carbamate as an impure yellow foam. Thin layer chromatography (TLC): R₁=0.74 in 9:1 CH₂Cl₂/MeOH. Gas chromatography—mass spectrometry showed the major peak with a molecular ion of 406 which is the molecular weight of the title compound.

EXAMPLE 7

5-(3[(2R)-exo-bicyclo[2.2.1]hept-2-yloxy]-4-methoxyphenyl)-3,4,5,6-tetrahydropyrimidin-2(1H)-one The crude bis-carbamate foam from Example 6 (98 mg, 0.2 mmol) was dissolved in MeOH (0.5 mL), treated with 0.5 mL of 25% NaOMe in MeOH, and refluxed for 18 hours. After removal of the solvent, the resulting solid was dissolved in water, extracted two times with CH₂Cl₂ and the combined organic layers dried over magnesium sulfate (MgSO₄). Filtration and concentration of the filtrate gave 48 mg (75%) of the desired urea as a yellow solid. Thin layer chromatography (TLC): R₁=0.57 in 9:1 CH₂Cl₂/MeOH.

We claim:

1. A process for preparing a compound of the formula

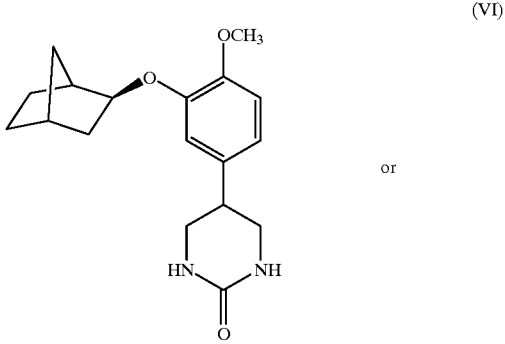

(VI)

or

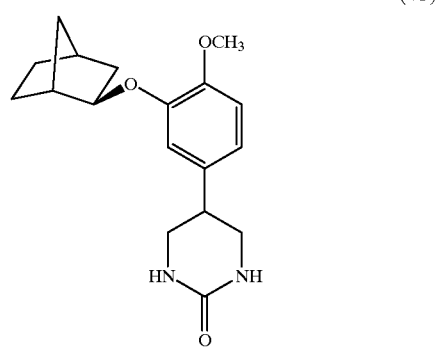

(VI')

comprising:

(a) reacting, respectively, a compound of the formula

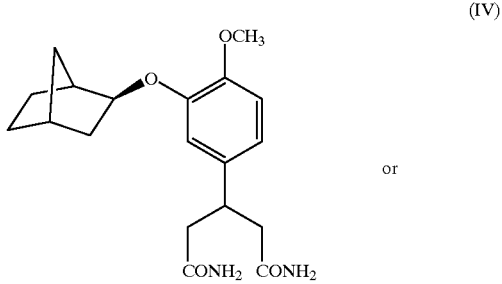

(IV)

or

-continued (IV')

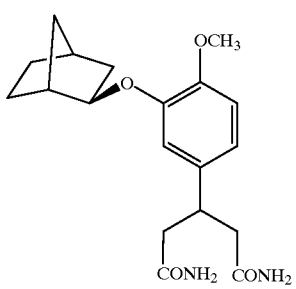

with diacetoxyIodobenzene, NaOZ and Z'OH, wherein Z and Z'are independently selected from hydrogen and $(C_1-C_6)$alkyl, to form an intermediate of the formula (V)

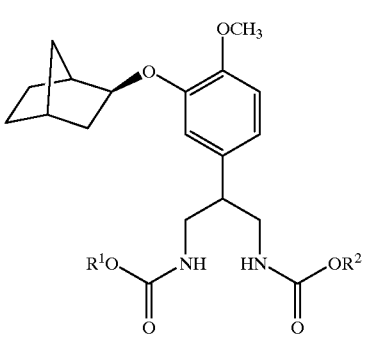

or (V')

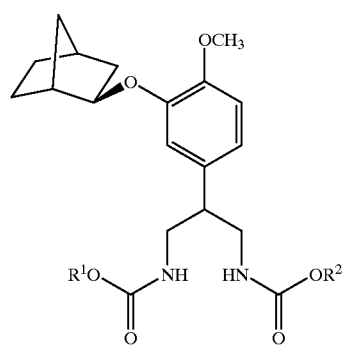

wherein $R^1$ and $R^2$ are independently selected from hydrogen and $(C_1-C_6)$alkyl; and then either:

(b1) isolating said intermediate of formula V or V' and reacting it with compounds of the formulae NaOZ and Z'OH, wherein Z and Z' are defined as above; or (b2) reacting said intermediate of formula V or V' in situ with compounds of the formula NaOZ and Z'OH, wherein Z and Z' are defined as above.

2. A process for preparing a compound of the formula (VI) or (VI') (VI)

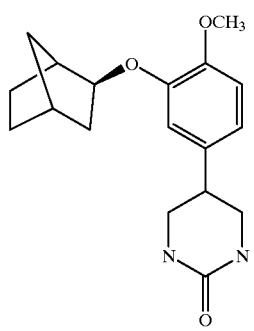

or (VI')

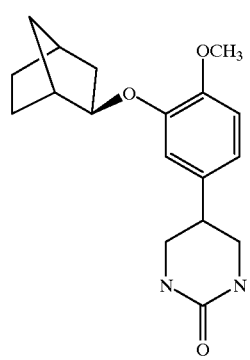

comprising:

(1) reacting 3-hydroxy-4-methoxybenzaldehyde with a compound of the formula $XCH_2CO_2H$, wherein X is —CN, —$CO_2$ $(C_1-C_6)$alkyl, —$CONH_2$ or —CONHOH, in the presence of a base, to form a compound of the formula (II')

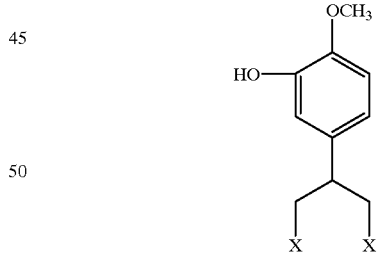

wherein X is as defined above; or (2) (a) reacting a compound of the formula II' wherein each X is —CN with hydrogen peroxide to form the corresponding bis-amide in which both —CN groups are replaced by —$CONH_2$; (b) subjecting the bis-amide formed in step (a) to a Hoffman rearrangement using an oxidizing agent to form the corresponding biscarbamate; and (c) reacting the biscarbamate formed in step (b) with a base to form a cyclic urea wherein X and X taken together forms a group of the formula

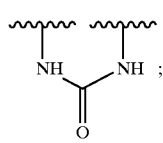
(a)

and then (3) reacting said compound of formula II' formed in step 1 or 2 above with a triaryl or trialkylphosphine, an azo dicarboxylate, and either R-(+)-endo-norborneol or S-(−)-endo-norborneol, respectively.

3. A process according to claim 2 wherein said base is a tertiary amine.

4. A process according to claim 2 wherein both a tertiary amine and a secondary amine are added to the reaction mixture.

5. A process according to claim 4 wherein the tertiary amine is selected from N-methylmorpholine, triethylamine, pyridine and diisopropyl amine and the secondary amine is selected from piperidine and pyrrolidine.

6. A process according to claim 2 wherein the azo dicarboxylate is selected from diisopropylazadicarboxylate and azodicarbonyldipiperidine.

7. A process according to claim 2 wherein the triarylphosphine is triphenylphosphine.

8. A process for preparing a compound of the formula

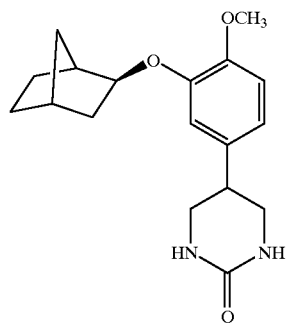
(VI)

or

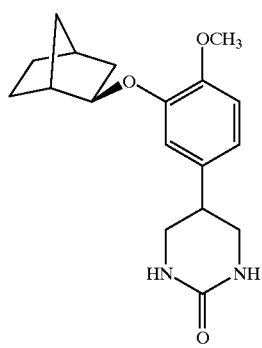
(VI')

comprising reacting, respectively, a compound of the formula

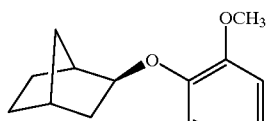
(V)

or

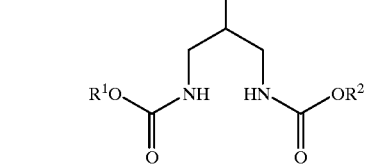
(V')

wherein $R^1$ and $R^2$ are independently selected from hydrogen and $(C_1-C_6)$alkyl, with compounds of the formulae NaOZ and Z'OH, wherein Z and Z' are independently selected from hydrogen and $(C_1-C_6)$alkyl.

9. A process for preparing a compound of the formula

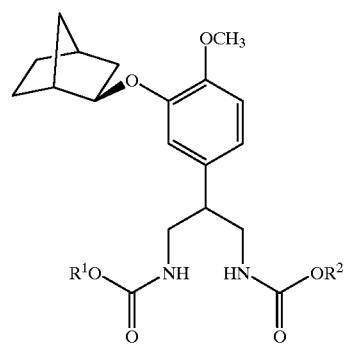
(II)

wherein X and Y, taken together, form a group of the formula.

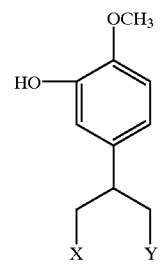
(a)

comprising:

(a) reacting a compound of the formula II wherein X and Y are both —CN with hydrogen peroxide to form the corresponding bis-amide in which both —CN groups are replaced by —CONH$_2$;

(b) subjecting the bis-amide formed in step (a) to a Hoffman rearrangement using an oxidizing agent to form the corresponding biscarbamate; and (c) reacting the biscarbamate formed in step (b) with a base to form a cyclic urea wherein X and Y taken together, form a group of the formula

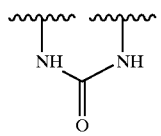

(a)

10. A process according to claim 9, wherein said base is a tertiary amine.

11. A process according to claim 9, wherein both a tertiary amine and a secondary amine are added to the reaction mixture.

12. A process according to claim 11, wherein said secondary amine is piperidine or pyrrolidine.

13. A process for preparing a compound of the formula.

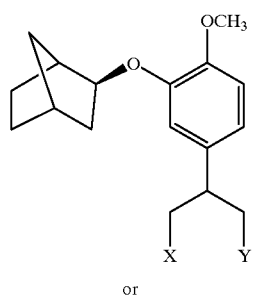

(III)

or

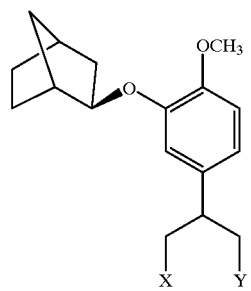

(III')

wherein X and Y, taken together, form a group of the formula

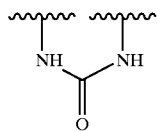

(a)

comprising (a) reacting a compound of formula (II)

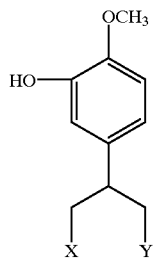

(II)

wherein X is —NHCOOR$^1$ and Y is —NHCOOR$^2$, where R$^1$ and R$^2$ are independently selected from (C$_1$–C$_6$)alkyl or hydrogen, with a base to form a compound of formula (II) wherein X and Y, taken together, form a group of the formula (a) above and (b) reacting the product of step (a) with a triaryl or trialkylphosphine, an azo dicarboxylate and either R(+)-endo-norbomeol or S-(−)-endo-norbomeol, respectively.

14. A process for preparing a compound of the formula (VI) or (VI')

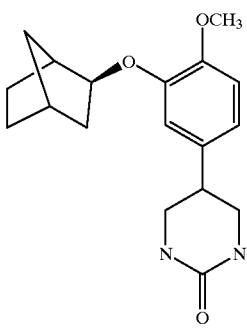

(VI)

or

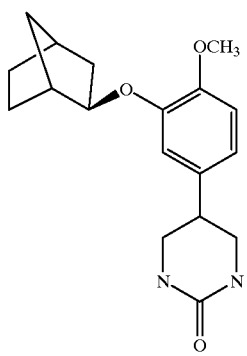

(VI')

comprising (a) reacting a compound of formula (II)

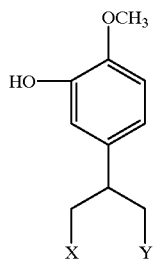

(II)

wherein X is —NHCOOR$^1$ and Y is —NHCOOR$^2$, where R$^1$ and R$^2$ are independently selected from (C$_1$–C$_6$)alkyl or hydrogen, with a base to form a compound of formula and (b) reacting said compound formed in step (a) above with a triaryl or trialkylphosphine, an azo dicarboxylate, and either R-(+)-endo-norborneol or (S)-(−)-endo-norborneol, respectively.

* * * * *